(12) United States Patent
Guzman et al.

(10) Patent No.: US 11,761,937 B2
(45) Date of Patent: Sep. 19, 2023

(54) APPARATUS AND METHOD FOR TRACE GAS DETECTION UTILIZING UNMANNED AERIAL VEHICLES

(71) Applicant: University of Kentucky Research Foundation, Lexington, KY (US)

(72) Inventors: Marcelo I. Guzman, Lexington, KY (US); Travis J. Schuyler, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 27 days.

(21) Appl. No.: 17/397,774

(22) Filed: Aug. 9, 2021

(65) Prior Publication Data
US 2021/0365025 A1    Nov. 25, 2021

Related U.S. Application Data

(62) Division of application No. 16/454,495, filed on Jun. 27, 2019, now abandoned.

(60) Provisional application No. 62/698,496, filed on Jul. 16, 2018.

(51) Int. Cl.
| | |
|---|---|
| *G01N 33/00* | (2006.01) |
| *G05D 1/00* | (2006.01) |
| *B64C 39/02* | (2023.01) |
| *G05D 1/10* | (2006.01) |

(52) U.S. Cl.
CPC ....... *G01N 33/0031* (2013.01); *B64C 39/024* (2013.01); *G01N 33/004* (2013.01); *G01N 33/0047* (2013.01); *G05D 1/0094* (2013.01); *G05D 1/101* (2013.01)

(58) Field of Classification Search
CPC .......... G01N 33/0047; G01N 33/0031; G01N 33/004; G05D 1/101; G05D 1/104; B64C 39/024
See application file for complete search history.

(56) References Cited

U.S. PATENT DOCUMENTS

| | | | |
|---|---|---|---|
| 10,866,226 B1* | 12/2020 | Smith | G01N 33/0036 |
| 2014/0166816 A1* | 6/2014 | Levien | G08G 5/0069 |
| | | | 244/175 |
| 2016/0084989 A1* | 3/2016 | Leclerc | G01N 21/59 |
| | | | 73/170.28 |
| 2016/0214715 A1 | 7/2016 | Meffert | |
| 2018/0284088 A1 | 10/2018 | Verbeck | |
| 2020/0064319 A1* | 2/2020 | McNulty | G01N 33/0044 |

* cited by examiner

*Primary Examiner* — Benjamin R Schmitt
(74) *Attorney, Agent, or Firm* — Stites & Harbison PLLC; Warren D. Schickli (57) ABSTRACT

An apparatus for trace gas detection includes an unmanned aerial vehicle and a sensor package including an ambient environmental parameter sensor and a gas sensor for trace gas detection. A trace gas detection system includes two such unmanned aerial vehicles and a ground station all adapted for monitoring ambient environmental parameters and trace gas detection.

11 Claims, 8 Drawing Sheets

APPARATUS AND METHOD FOR TRACE GAS DETECTION UTILIZING UNMANNED AERIAL VEHICLES

RELATED APPLICATION

This application is a Divisional Application of U.S. application Ser. No. 16/454,495, having a filing date of Jun. 27, 2019, which claims priority to U.S. Provisional Patent Application 62/698,496, filed Jul. 16, 2018, which is hereby incorporated by reference in its entirety.

GOVERNMENT SUPPORT

This invention was made with government support under grant No. 1539070 awarded by the U.S. National Science! Foundation under RII Track-2 FEC. The government has certain rights in the invention.

TECHNICAL FIELD

This document relates generally to the field of trace gas detection and, more particularly, to an apparatus and method for detecting, quantifying and GPS-locating trace gases using unmanned aerial vehicles while simultaneously measuring ambient temperature, relative humidity and barometric pressure.

BACKGROUND

A new and improved apparatus, system and method are provided for detecting, quantifying and GPS-locating trace gases utilizing unmanned aerial vehicles (UAVs) from 0-100 meters above ground level for up to one hour or more while simultaneously measuring ambient temperature, relative humidity and barometric pressure. The apparatus, system and method are useful to identify point source pollution events (such as leaks at natural gas transportation storage facilities and coal powered power plants) as well as general environmental monitoring. Advantageously, the apparatus, system and method are also useful for economical, periodic monitoring of ambient air quality as well as for estimating the impacts of the large pollution events such as natural gas leaks by quantifying the trace gases released. More particularly, the apparatus, system and method are capable of detecting both anthropogenic and biogenic sources of pollution. The apparatus, system and method are also able to detect greenhouse and toxic gases and can be configured in many different ways to provide numerous combinations of gas detection. The apparatus, system and method may also be utilized in other fields such as for the detection of methane produced by methane tundra bogs.

SUMMARY OF THE INVENTION

In accordance with the purposes and benefits described herein, a new and improved apparatus is provided for trace gas detection. That apparatus comprises an unmanned aerial vehicle (UAV) including a receiver and a sensor package held on a support carried in the receiver. That sensor package may include at least one ambient environmental parameter sensor for detecting current temperature, current relative humidity and current barometric pressure and at least one gas sensor for detecting in real time the presence of at least two gases to be monitored by the apparatus.

In one or more of the many useful embodiments of the apparatus, the at least one gas sensor is configured to detect the presence of at least two gases from a group of gases including methane, propane and butane. In at least one possible embodiment of the apparatus, the at least one gas sensor is configured to detect the presence of methane, propane and butane. In at least one possible embodiment of the apparatus, the at least one gas sensor is configured to detect the presence of carbon dioxide and carbon monoxide. Further, in at least one of the many possible embodiments of the apparatus, the at least one gas sensor is further configured to detect a volatile organic compound (VOC).

In many of the possible embodiments of the apparatus, the apparatus further includes a GPS locator device providing real time location coordinates for the UAV.

In accordance with an additional aspect, a new and improved trace gas detection system is provided. That trace gas detection system comprises a first UAV including a first sensor package having a first environmental parameter sensor for detecting current temperature, current relative humidity and current barometric pressure and a first gas sensor for detecting in real time the presence of at least one gas to be monitored by the trace gas detection system. In addition, the trace gas detection system includes a second UAV including a second sensor package having a second ambient environmental parameter sensor for detecting current temperature, current relative humidity and current barometric pressure and a second gas sensor for detecting in real time the presence of the at least one gas to be monitored by the trace gas detection system. As should be appreciated, the trace detection system provides for gas detection simultaneously at two points within an area to be monitored by the trace gas detection system.

In at least one of the many possible embodiments of the trace gas detection system, the first gas sensor and the second gas sensor are configured to detect the presence of at least two gases from a group of gases including methane, propane and butane.

In at least one of the many possible embodiments, the first gas sensor and the second gas sensor are configured to detect the presence of methane, propane and butane.

In at least one possible embodiment of the trace gas detection system, the first gas sensor and the second gas sensor are configured to detect the presence of carbon dioxide and carbon monoxide.

In one or more of the many possible embodiments, the first gas sensor and the second gas sensor may be further configured to detect a volatile organic compound (VOC).

The first UAV of the trace gas detection system may include a first GPS locator device providing real time location coordinates for the first UAV. Similarly, the second UAV may include a second GPS locator device providing real time location coordinates for the second UAV.

Still further, the trace gas detection system may further include a ground station. That ground station may include a third sensor package having a third ambient environmental parameter sensor for detecting current temperature, current relative humidity and current barometric pressure and a third gas sensor for detecting in real time the presence of the at least one gas to be monitored by the trace gas detection system. In this way, the trace gas detection system is adapted to simultaneously provide gas detection at three points within the area being monitored.

In accordance with still another aspect, a new and improved method of monitoring an area for gas detection is provided. That method comprises the steps of: (a) flying a first unmanned aerial vehicle (UAV) with a first sensor package on a first flight profile through the area, (b) simultaneously flying a second UAV with a second sensor package on a second flight profile through the area, (c) monitoring the current location of the first UAV by a first GPS locator and monitoring the current location of the second UAV by a second GPS locator and (d) simultaneously detecting the presence of the at least one gas of interest with the first sensor package and the second sensor package.

The method may further include the step of providing the first profile along a first axis through the area and providing the second profile along a second, different axis through the area. That first axis may be vertical while the second axis may be horizontal.

Still further, the method may include the step of detecting current ambient temperature, real humidity and barometric pressure by operation of a first ambient parameter sensor on the first UAV and a second ambient parameter sensor on the second UAV.

In addition, the method may further include the step of locating a ground station with a third sensor package within the area. In such an embodiment, the method may further include the step of simultaneously detecting the presence of the at least one gas of interest with the first sensor package, the second sensor package and the third sensor package whereby gas detection is simultaneously provided at three different locations within the area.

Still further, the method may include the step of detecting current ambient temperature, real humidity and barometric pressure by operation of a third ambient parameter sensor on the ground station.

In the following description, there are shown and described several preferred embodiments of the apparatus, trace gas detection system and method of monitoring an area for gas detection. As it should be realized, the apparatus, trace gas detection system and method are capable of other, different embodiments and their several details are capable of modification in various, obvious aspects all without departing from the apparatus, system and method as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the specification, illustrate several aspects of the apparatus, trace gas detection system and method, and together with the description serves to explain certain principles thereof.

Reference will now be made in detail to the present preferred embodiments of the apparatus, the trace gas detection system and the method, examples of which are illustrated in the accompanying drawing figures.

DETAILED DESCRIPTION

Figure 1:
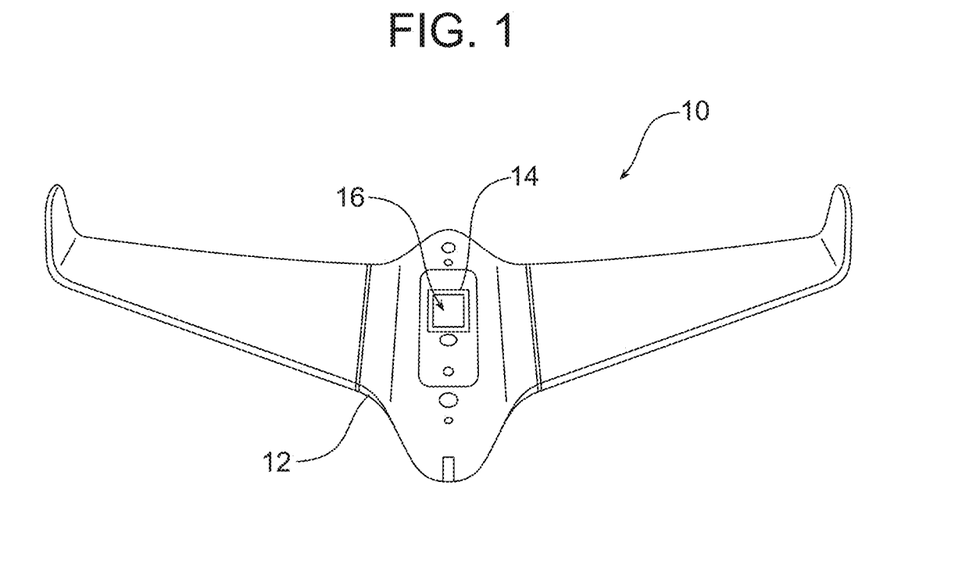
FIG. 1 is a perspective view of an unmanned aerial vehicle of the apparatus for trace gas detection.
Figure 2:
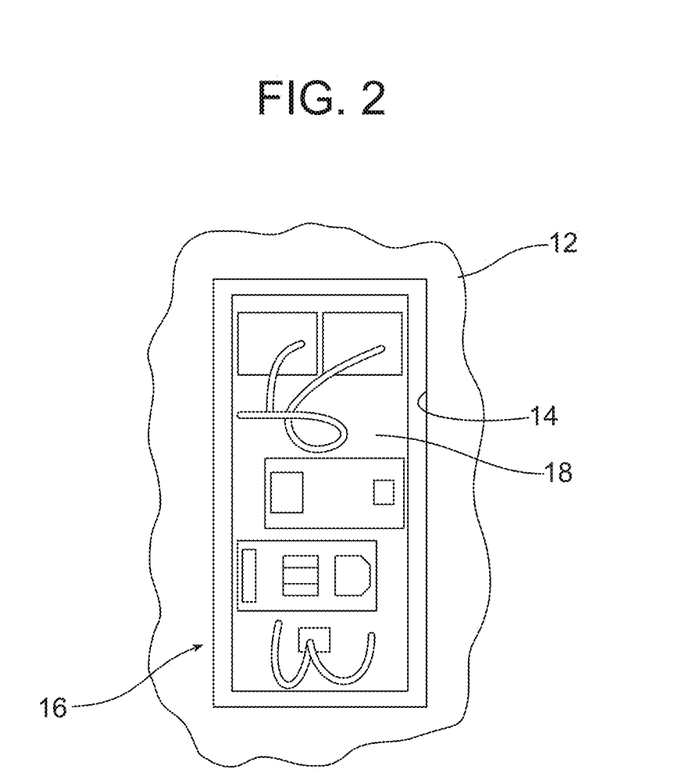
FIG. 2 is detailed illustration of the unmanned aerial vehicle of FIG. 1 illustrating the sensor package held in the receiver of the unmanned aerial vehicle.
Figure 3:
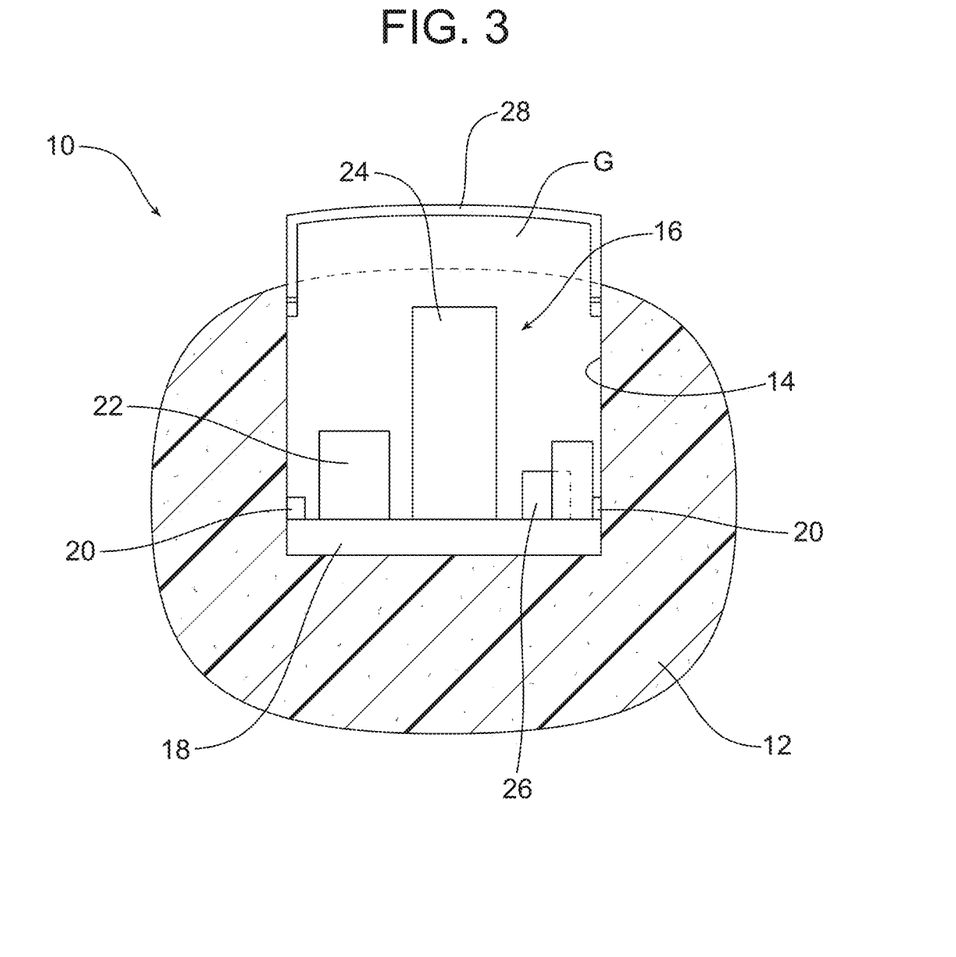
FIG. 3 is a detailed view of the sensor package and radiation shield.

Reference is now made to FIGS. 1-3 illustrating a new and improved apparatus 10 for trace gas detection. As illustrated in FIG. 1, the apparatus 10 includes an unmanned aerial vehicle (UAV) 12 incorporating a receiver 14. A sensor package 16 is held on a support 18 carried in the receiver 14. A releasable latching system 20, of a type known in the art, may be utilized to secure the support 18 and the sensor package 16 in the receiver. One may release the latching system 20 to service or replace the sensor package 16 as required depending on the particular application for which the apparatus 10 is to be utilized at any given time.

As further illustrated and explained below, the sensor package 16 may include at least one ambient environmental parameter sensor 22 for detecting current ambient temperature, relative humidity and barometric pressure and at least one gas sensor 24 for detecting in real time the presence of at least two gases to be monitored by the apparatus 10. In one particularly useful embodiment, the at least one gas sensor 24 is configured to detect the presence of at least two of the gases selected from a group of gases including methane, propane and butane. In at least one possible embodiment, the at least one gas sensor 24 is configured to detect the presence of all three of these gases.

In other possible embodiments of the apparatus 10, the at least one gas sensor 24 is configured to detect the presence of carbon dioxide and carbon monoxide. In still other possible embodiments, the at least one gas sensor is configured to detect the presence of a volatile organic compound (VOC) of interest to the researcher. Volatile organic compounds that may be monitored include but are not necessarily limited to methane, propane, butane and non-methane VOCs, and combinations thereof.

As further illustrated in FIGS. 1-3, the apparatus 10 may also include a global positioning system (GPS) locator device 26 providing real time location coordinates for the UAV 12 as it travels along a flight path through an area in which it is desired to provide for trace gas detection.

As shown in FIG. 3, the sensor package 16 held in the receiver 14 may be protected from solar radiation by an overlying radiation shield 28 that may be connected to the body of the aerial vehicle 12 by spring clips or other fasteners not shown. An air gap G between the body of the aerial vehicle 12 and the shield 28 ensures good air flow past the environmental parameter and gas sensors 22, 24 as the aerial vehicle 12 flies thereby ensuring collection of accurate readings not skewed by variations in solar radiation experienced at any time during data collection.

In the embodiment illustrated in FIGS. 1-3, the UAV 12 is a fixed wing vehicle adapted to fly a horizontal flight profile. A Skywalker X8 fixed wing vehicle is one off-the-shelf product useful for this purpose. While not illustrated in FIGS. 1-3, it should also be appreciated that the UAV may be adapted for flying a vertical flight profile. A DJI Phantom III quadcopter is just one such off the shelf vehicle useful for this purpose.

Figure 4:
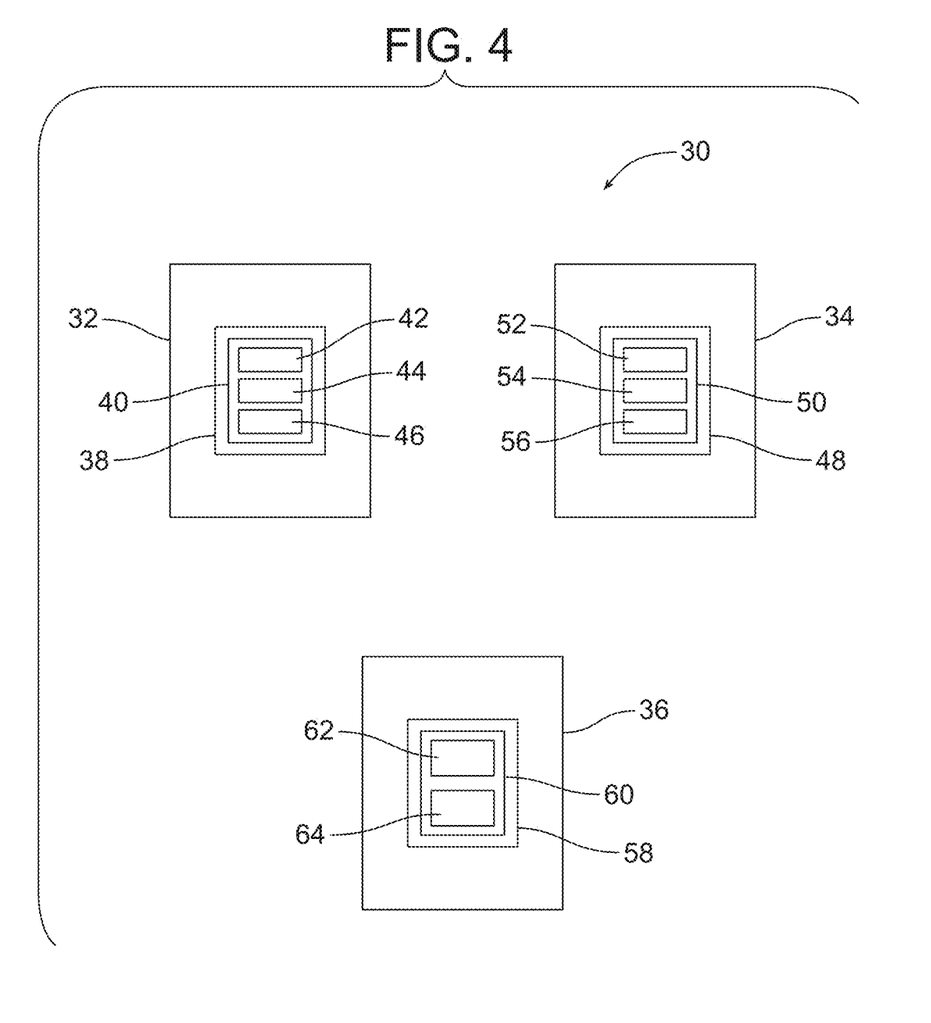
FIG. 4 is a schematic illustration of the trace gas detection system including a first unmanned aerial vehicle, a second unmanned aerial vehicle and a ground station.

Reference is now made to FIG. 4 illustrating a new and improved trace gas detection system 30 for atmospheric monitoring of trace atmospheric gases. More particularly, the trace gas detection system 30 is particularly useful for accurately quantifying dynamic emissions in the proximity of pollution sources under wind turbulence including the large bandwidth of turbulent flow experienced at the surface of the earth: that is in the lowest few hundred meters of the atmospheric boundary layer. Advantageously, the trace gas detection system 30 may be utilized for a number of useful applications including in the detection of fugitive greenhouse gases such as methane, carbon dioxide, nitrous oxide and hydrofluorocarbons from transportation, industry and livestock as well as other pollutants such as carbon monoxide, ammonia, sulfur dioxide, various nitrogen oxides and various volatile organic compounds of interest.

As illustrated in FIG. 4, the trace gas detection system 30 includes a first unmanned aerial vehicle 32, a second unmanned aerial vehicle 34 and a ground station 36. In the illustrated embodiment the first UAV 32 is a quadcopter adapted for flying a first or vertical flight profile while the second UAV 34 is a fixed wing adapted for flying along a second, horizontal flight profile through the area in which trace gases are to be detected. The ground station 36 is positioned on the ground, and can be placed near the middle of the area in which the gases are to be detected. Alternatively, the ground station 36 can be positioned outside the area in which the gases are to be detected to provide reference.

As schematically illustrated in FIG. 4, the first UAV 32 includes a first receiver 38 that receives and holds a first sensor package 40 including a first environmental parameter sensor 42 for detecting current ambient temperature, current ambient relative humidity and current ambient barometric pressure and a first gas sensor 44 for detecting in real time the presence of at least one gas to be monitored by the trace gas detection system. A first GPS locator device 46 carried on the first UAV 32 allows one to continuously monitor the position of the first UAV during operation.

The second UAV 34 includes a second receiver 48 for receiving and holding a second sensor package 50 including a second environmental parameter sensor 52 for detecting current ambient temperature, current ambient relative humidity and current ambient barometric pressure and a second gas sensor 54 for detecting in real time the presence of the at least one gas to be monitored by the trace gas detection system. A second GPS locator device 56 carried on the second UAV 34 allows one to continuously monitor the location of the second UAV during operation.

The ground station 36 includes a receiver 58 adapted to receive and hold a third sensor package 60 including a third ambient environmental parameter sensor 62 for detecting current ambient temperature, current ambient relative humidity and current barometric pressure and a third gas sensor 64 for detecting in real time the presence of the at least one gas to be monitored by the trace gas detection system. The ground station 36 may also include a third GPS Locator device, not shown. Advantageously, the trace gas detection system 30 illustrated in FIG. 4 allows for simultaneous gas detection at three points within an area being monitored for the trace gas in question. The environmental parameter sensors 42, 52 and 62 allow for continuous monitoring of current ambient temperature, relative humidity and barometric pressure at the current positions of each gas sensor 44, 54, 64 throughout the trace gas detection process thereby allowing trace gas detection measurements by the gas sensors to be adjusted for any fluctuations in the environmental factors that might skew any gas sensor readings. Correction factors are also provided for the air speeds of the UAVs 32 and 34.

Consistent with the above description, the trace gas detection system 30 may be utilized for a number of applications. Thus, in some embodiments, the first gas sensor 44, the second gas sensor 54 and the third gas sensor 64 are all configured to detect the presence of at least two of the gases of the group of gases including methane, propane and butane. In some embodiments the first gas sensor 44, the second gas sensor 54 and the third gas sensor 64 are configured to detect the presence of all three of these gases.

In some other embodiments, the first gas sensor 44, the second gas sensor 54 and the third gas sensor 64 are configured to detect the presence of carbon dioxide and carbon monoxide. In some embodiments of the trace gas detection system 30, the first gas sensor 44, the second gas sensor 54 and the third gas sensor 64 are configured to detect a volatile organic compound (VOC) of interest. These are just some examples of how the gas sensors 44, 54, 64 may be configured and it should be appreciated that for other applications, the gas sensors may be configured to detect other gases of interest. In any of the embodiments, the receivers 38, 48, and 58 allow one to remove the sensor packages 40, 50, 60 and replace them with other sensor packages adapted to detect a trace gas of interest to the next application for which the trace gas detection system 30 is to be utilized. Thus, it should be appreciated that the trace gas detection system 30 may be quickly configured for a wide range of uses as desired by the operator.

Figure 5A:
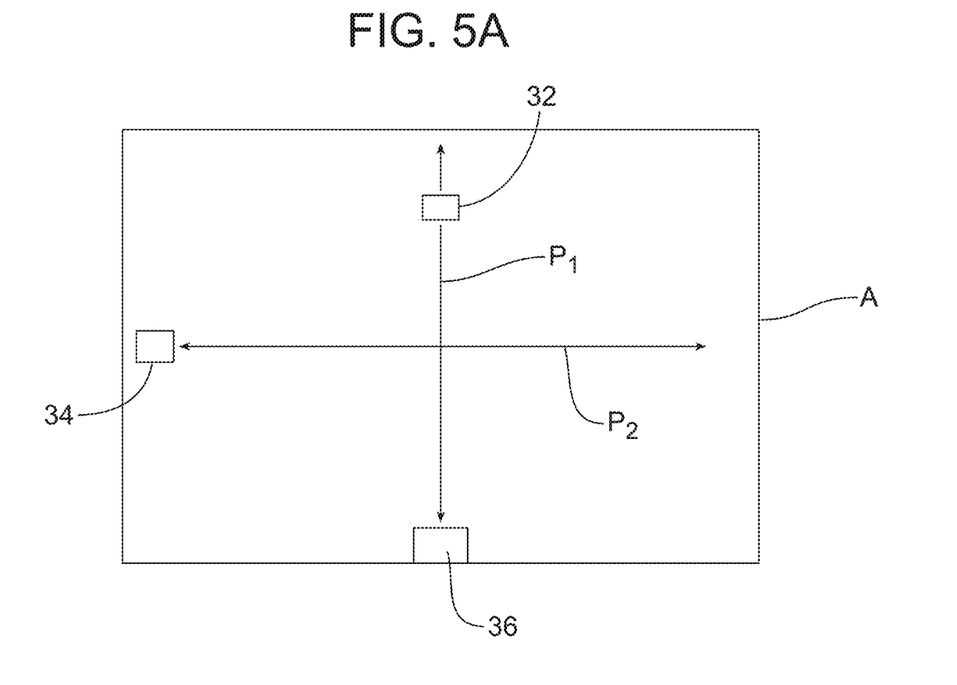
FIG. 5a is a schematic side view illustrating the trace gas detection system used in the method of monitoring an area for gas detection.
Figure 5B:
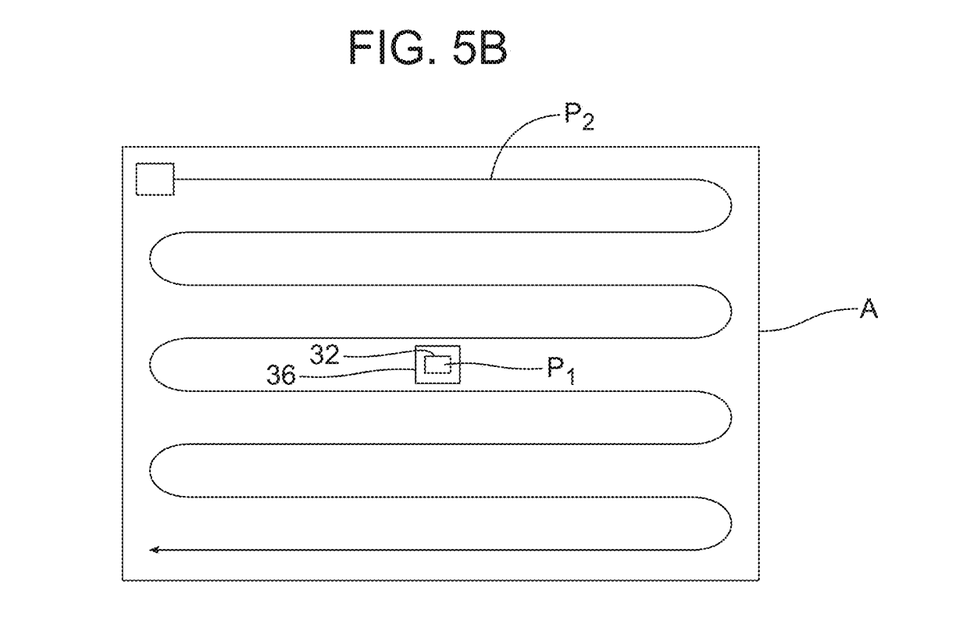
FIG. 5b is a schematic top plan view of the trace gas detection system used in the method of monitoring an area for gas detection.

The trace gas detection system 30 is useful in a method of monitoring an area A for gas detection including the steps of: (a) flying the first UAV 32 with the first sensor package 40 on a first flight profile $P_1$ through the area, (b) simultaneously flying the second UAV 34 with the second sensor package 50 on a second flight profile $P_2$ through the area and (c) monitoring the current location of the first UAV with the first GPS locator 46 and the second UAV with the second GPS locator 56. In addition, the method includes simultaneously detecting the presence of at least one gas of interest with the first sensor package 40 on the first UAV 32 and the second sensor package 50 on the second UAV 34. The method may also include detecting current ambient temperature, ambient relative humidity and barometric pressure by operation of the first environmental parameter sensor 42 and the second environmental parameter sensor 52. In the embodiment illustrated in FIGS. 5A and 5B, the first profile $P_1$ is along a vertical axis while the second profile $P_2$ is along the horizontal axis.

Where the trace gas detection system 30 being utilized includes the ground station 36, the method may further include locating the ground station with the third sensor package 60 within the area and simultaneously detecting the presence of the at least one gas of interest with all three sensor packages 40, 50, 60 so that gas detection is simultaneously provided at three different locations within the area. Similarly, the method may include the step of detecting current ambient temperature, current ambient relative humidity and current ambient barometric pressure by operation of the third ambient parameter sensor 62 at the ground station 36.

As should be appreciated, by continuously monitoring ambient temperature, relative humidity and barometric pressure at three different locations in the area while simultaneously detecting a trace gas of interest at three different locations in the area it is possible to closely pinpoint the source location of the trace gas.

Experimental Example

The following hardware was used to create the trace gas detection system with unmanned vehicles
Arduino UNO microcontroller
SEEED Studio V2 Base Shield
Mayhew Labs Extended ADC Shield
Arduino Wireless SD Shield
Xbee wireless transmitter XB3-24Z8PT
Sandisk Ultra Class 10 8 GB microSD card
ThunderPower RC 2S 1350 mAh battery
Bosch BME280, on a Grove PCB
Mocon Baseline piD tech eVx photoionization sensor (blue, non-methane VOC)
Grove WSP2110 (HCHO/total VOC) sensor
SEEED Studio MH-Z16 Carbon Dioxide Sensor
MiCS-6814 (Multichannel Gas Sensor), on a Grove PCB
MQ3 (Methane) Gas Sensor, on a Grove PCB
MQ131 (Ozone) Gas Sensor, on a SainSmart PCB
Push Button
LED The application can be upgraded by substituting the hardware above with newer components.

Operative/Preferred Process Parameters
Assembly:
Plug the Arduino UNO microcontroller into a power source. Use a volt meter to find the input voltage on the bottom side of the circuit board where the Arduino connects to the power cord. Solder wires to the appropriate pins and fabricate an adapter for the 2S 1350 mAh battery. Plug the battery into the Arduino and make sure the power source is stable. Unplug device from power source for the remainder of assembly.

Place V2 Base Shield on top of the Arduino UNO microcontroller. Plug the MiCS-6814 and Bosch BME280 sensors into respective I2C ports. Plug the MH-Z16 sensor into a digital connection. Plug the push button into another digital slot, and the LED in a third digital port. Place the piD photoionization sensor, the WSP2110 sensor, the MQ3 sensor, and the MQ131 sensor into 4 respective analog ports. Remove the analog signal wire from each of the connections, ensuring the power connections are not disturbed. Place each of the analog wires into the respective connection in the ADC shield. Place the ADC Shield on top of the V2 Base Shield.

Place the Wireless SD Shield on top of the ADC Shield. Place the Xbee wireless transmitter into its dedicated position on top of the Wireless SD Shield. Insert the Sandisk Ultra Class 10 8 GB microSD card into the Wireless SD Shield.

Place the device into a (3D printed) enclosure and secure package to the UAV.

Operation:
Plug a USB printer cable into the Arduino UNO and into the laptop to upload the code. Once the code is successfully uploaded, the LED will illuminate and the device will begin collecting and storing data at 1 Hz. Plug the battery into the Arduino, and remove the device from the computer. The device operates at 5V, in environmentally relevant weather conditions (excluding relative humidities of 100%), for up to 6 hours. Data collection can be started and stopped with the push button. Device data collection mode is indicated with LED illumination that is visible while device is on the UAV. It is highly suggested that the user calibrates each sensor in the laboratory (as described below) for most accurate measurements on the UAV.

Sensor Package Specifications
Below are the relevant sensor specifications for the trace gas and meteorological sensors. Table S1 includes the operating range, accuracy, precision, and resolution of the trace gas sensors. Table S2 has the specification provided for the temperature, pressure, and relative humidity sensors.

TABLE S1

Relevant Gas Sensor Specifications.

| Gases | Operating Range (ppbv) | Accuracy (% of measured value) | Precision (ppbv) | Resolution (ppbv) |
|---|---|---|---|---|
| Methane | 1000-6000 | ±1.24% | 180 | 10 |
| Ammonia | 500.0-9040 | ±0.20% | 30 | 10 |
| Carbon Dioxide | 80,000-1,622,000 | <±1% | <2000 | 1000 |
| Propane | 52,630-264,200 | ±0.71% | 520 | 10 |
| Butane | 52,030-264,200 | ±0.45% | 380 | 10 |
| Carbon Monoxide | 52,030-264,200 | ±0.52% | 580 | 10 |

TABLE S2

Meteorological Sensor Specifications.

| Gases | Accuracy | Precision | Response Time |
|---|---|---|---|
| Temperature | ±1.0° C. | ±0.005° C. | 0.5 sec to 66% full signal |
| Pressure | ±1.0 hPa | ±0.002 hPa | — |
| Relative Humidity | ±3% | ±2% | 1 sec to 63% of full signal |

Figure 6:
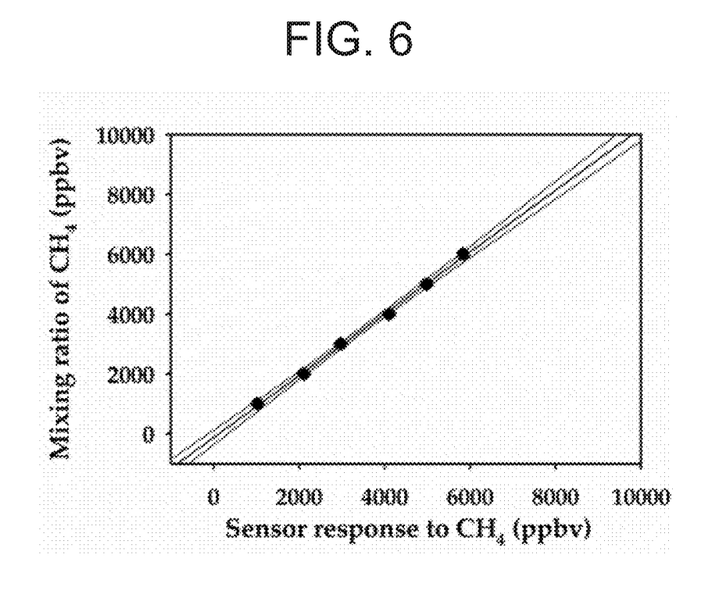
FIG. 6 is a methane calibration curve from 1,000-6,000 ppbv. y=1.033(x)−122.0, where y represents the concentration of the gas of interest (in parts per billion by volume of air) and x represents the response of the sensor. The coefficient of determination for the straight line is $R^2=0.9981$.
Figure 7:
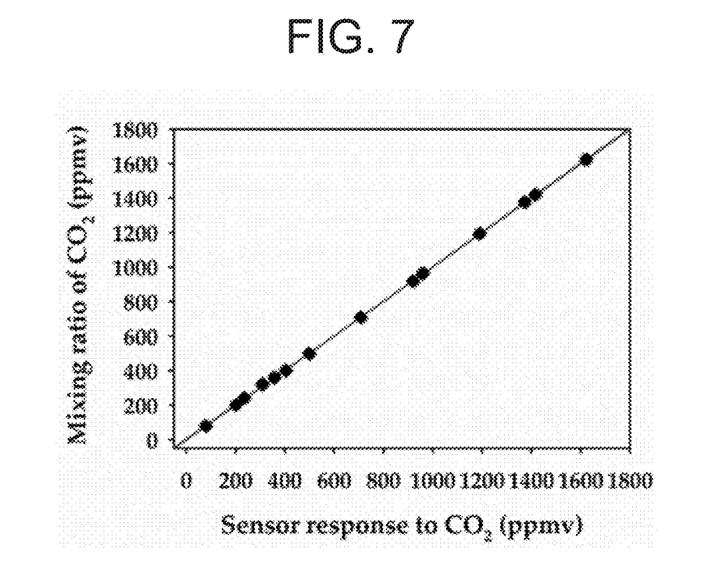
FIG. 7 is a carbon dioxide calibration curve from 80.00-1622 ppmv. y=0.9993x−1.682, where y represents the concentration of the gas of interest (in parts per billion by volume of air) and x the response of the sensor. The coefficient of determination for the straight line is $R^2=0.9999$.
Figure 8:
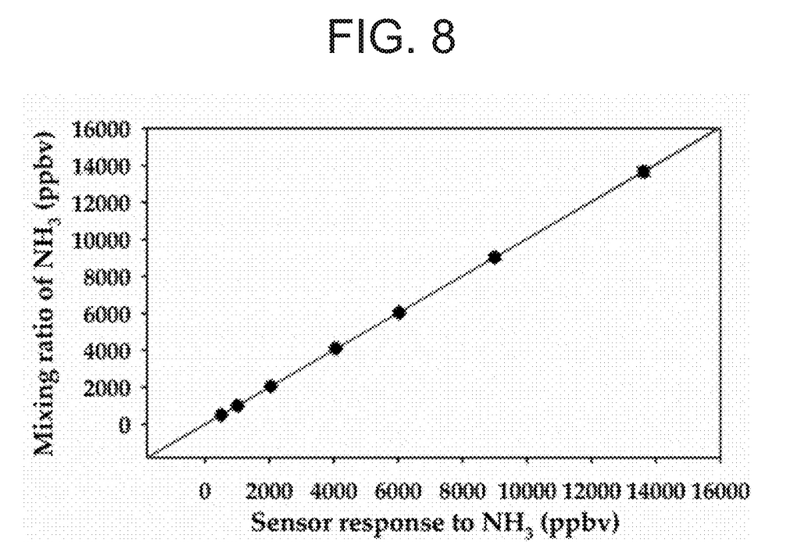
FIG. 8 is an ammonia calibration curve from 500.0-9040 ppbv. y=1.003(x)−0.0037, where y represents the concentration of the gas of interest (in parts per billion by volume of air) and x the response of the sensor. The coefficient of determination for the straight line is $R^2=0.9999$.

The calibration curves S1, S2, and S3 for the methane ($CH_4$), carbon dioxide ($CO_2$), and ammonia ($NH_3$) gas sensors are provided respectively in FIGS. 6, 7 and 8. Methane and carbon dioxide gas sensors were calibrated using primary certified gas and certified calibrated mass flow controllers. This provided confidence of ±1% of the requested gas concentration. The gas sensors were calibrated in an environmental chamber where the gas composition, temperature and relative humidity were controlled.

The ammonia calibrations were achieved by using the custom environmental chamber. In brief, it is a sealed chamber that allows for total control of atmospheric composition. The ammonia vapor produced by ammonium hydroxide solutions of various volumes were used to calculate the theoretical ppbv of ammonia gas in the chamber. The stock ammonium hydroxide solution was 29.28%, or 15.45 M. Ammonium hydroxide forms ammonia and water as described in the acid base reaction below. The $K_b$ of the reaction is provided in Equation 1.

$$NH_3(g)H_2O(l) \rightleftharpoons NH_4^+(aq) + HO^-(aq). \quad \text{Reaction 1}$$

$$K_b = \frac{[NH_4^+][HO^-]}{[NH_3]} = 1.89 \times 10^{-5}. \quad \text{Eqn. 1}$$

The mole fraction of free $NH_3$ in solution was calculated using the $pK_a$ and pH of the solution at 24° C., and described in Equation 2.

$$NH_3(aq) = [10^{(pK_a - pH)} + 1]^{-1} \quad \text{Eqn 2.}$$

Given that the pH of the 15.45 M stock solution was 11.60, 99.53% of the ammonium hydroxide was present as ammonia. Next, the partial pressures of ammonia and water were used to calculate the mass fraction of ammonia present as vapor above the solution. The fraction was multiplied by the mass of ammonium hydroxide in solution and converted in μg. The mass was converted to ppbv by dividing the μg of ammonia vapor by the volume of the chamber in L to get ppbv. The calibration curve for the ammonia sensor is shown in FIG. 8.

Figure 9:
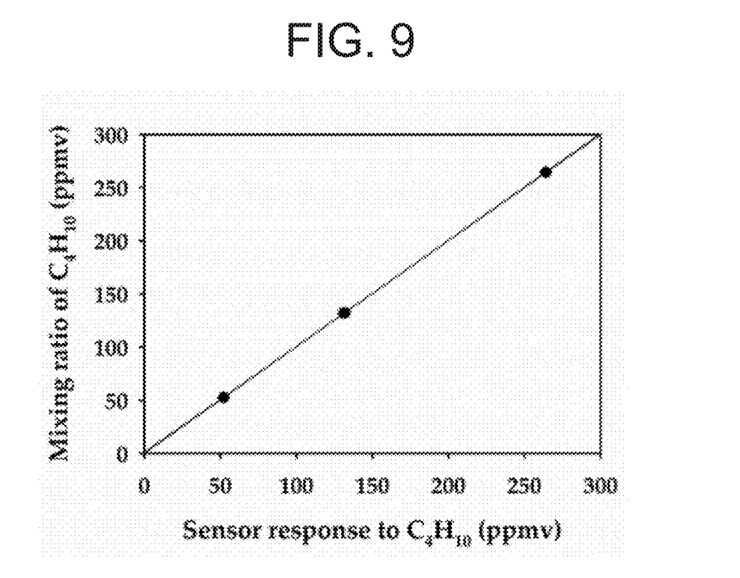
FIG. 9 is a butane calibration curve from 52.03-264.2 ppmv. y=0.9980(x)−0.6771, where y represents the concentration of the gas of interest (in parts per billion by volume of air) and x the response of the sensor. The coefficient of determination for the straight line is $R^2=0.9999$.
Figure 10:
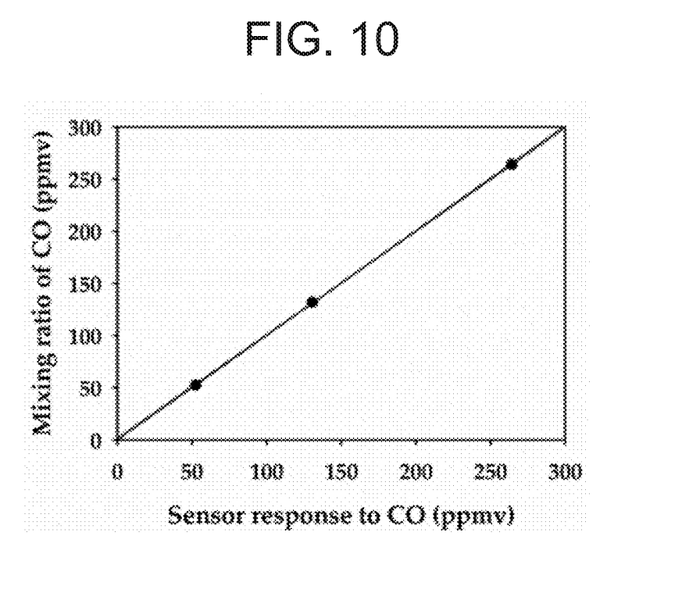
FIG. 10 is a carbon monoxide calibration curve from 52.03-264.2 ppmv. y=0.9982(x)−0.8433, where y represents the concentration of the gas of interest (in parts per billion by volume of air) and x the response of the sensor. The coefficient of determination for the straight line is $R^2=0.9999$.
Figure 11:
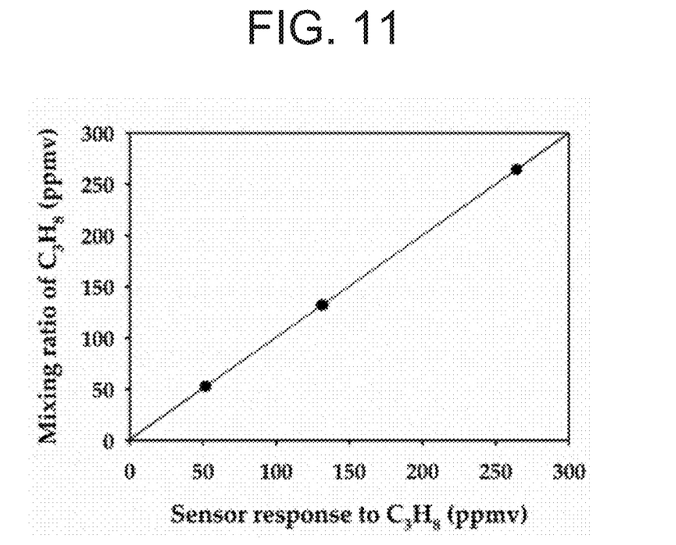
FIG. 11 is a propane calibration curve from 52.03-264.2 ppmv. y=0.9623(x)−1.069, where y represents the concentration of the gas of interest (in parts per billion by volume of air) and x the response of the sensor. The coefficient of determination for the straight line is $R^2=0.9999$.

In FIGS. 8, 9 and 10 the respective calibration curves for propane ($C_3H_8$), butane ($C_4H_{10}$), and carbon monoxide (CO) are shown. The sensors were calibrated in the same environmental chamber described above. These (3) calibration curves cover a concentration range of 52.03-264.2 ppmv.

Experimental Methods

Description of Campaign Site

All research flights were performed in accordance with current regulations (Part 107) established by the United States of America Federal Aviation Authority (FAA). The flights took place at the Unmanned Aircraft Flight Station of Oklahoma State University (317 m above sea-level), which is located ~20 km to the east of Stillwater in the state of Oklahoma (36° 09' 43" N, −96° 50 07" W). The site is 23.72 km from Station 89 (STIL) of the Mesonet network, which is used for ground based measurements and sensor validation. The average wind speed at 2 m above ground level (AGL) registered on day one was 2.75 (±1.37) m s$^{-1}$, with the wind direction of 7° N. On day two, the average wind speed at 2 m AGL was 4.04 (±1.09) m s$^{-1}$, blowing 8° N.

Description of Flight Patterns

Two different UAVs were flown simultaneously along different flight patterns to demonstrate a method capable of collecting data needed for box models describing the concentration of trace gases. A DJI Phantom 3 quadcopter was flown manually to register vertical profiles, while a Skywalker X8 was flown on autopilot for horizontal profiles. Vertical profiles data from 10 to 120 m AGL was reported for ascent and descent rates of 3.0 m s$^{-1}$. Battery changes every 15 minutes were performed to extend the flying time to 1 hour.

Gas Sensing Packages

Three portable gas sensing packages were developed to monitor the mixing ratio of $NH_3$, CO, $NO_2$, $CH_4$, $C_3H_8$, $C_4H_{10}$, and $CO_2$. A package with microelectromechanical semiconductor (MEMS) sensors allowed monitoring simultaneously the gases $NH_3$, CO, and $NO_2$ with three independent channels. Similarly, the second package measured $CH_4$, $C_3H_8$, and $C_4H_{10}$. The third package quantified $CO_2$ levels with a nondispersive infrared detector (NDIR). The payload for the first, second, and third sensing packages were 227, 230, and 181 g, respectively.

A 10-bit microcontroller (Arduino) with a V2 Base Shield (SEEED Studio) and a Wireless SD Shield (Arduino) operating at 5.0 V were used to control the sensing packages. Up to 6 h of continuous operation was provided with a 1350 mA h battery (Thunder Power RC 2S). The data collection set at a rate of 1 Hz was started and stopped with a push-button. The illumination of a light emitting diode (LED) was used to confirm successful data logging for storage of files in CSV format to a microSD card with 8 GB capacity (SanDisk Ultra Class 10). Temperature, pressure and percent relative humidity were measured with a BME280 sensor (Bosch) with data transmitted via the I2C channel. The mixing ratios for $NH_3$, CO, $NO_2$, $CH_4$, $C_3H_8$, and $C_4H_{10}$ were measured with an analog MiCS-6814, a 3-channel MEMS semiconducting sensor. For $CO_2$ monitoring, a digital MH-Z16 NDIR sensor was utilized. The operation of the packages was enabled by writing customized codes for the sensors listed. The gas sensing elements were housed and protected from UV radiation in a 3D printed enclosure made of polylactic acid. After powering on the sensing packages and re-uploading the code, a time stamp was created. Warm-up and equilibration of the sensors was allowed for at least 1 h before take-off. The results reported below correspond to flights with identical gas sensing packages placed inside the Skywalker X8 and underneath the DJI Phantom 3. For data recovery, the devices were powered down before removing the SD cards.

Correction for Variable Air Speed and Solar Irradiation

A series of control flights were used to demonstrate that the response of the factory calibrated sensor packages, shielded underneath the DJI P3 quadcopter, are in excellent agreement with readings at the ground station. The previous controls discarded any possible distortion on the reading of the sensors due to air speed (meaning the rate of motion of the UAV relative to air) or solar irradiation. Small temperature variations were demonstrated not to affect the readout of other sensor packages, what discarded the need for any dynamic in-situ temperature correction due to temperature fluctuations within a flight. However, a systematic deviation of the response of sensor packages due to air speed and solar irradiation was identified for the Skywalker X8 fixed wing sUAS.

Systematic testing allowed us to conclude that the modified behavior onboard the Skywalker X8 was largely created by the air scoop generated over the UV radiation shield enclosing the sensor packages located on top of the aircraft, together with a minor contribution from solar irradiation. Thus, a two-stage set of laboratory controls was designed to correct the response of sensors for the variable air speed and solar irradiation conditions experienced by the sensor packages onboard the Skywalker X8 during flights. During the first set of controls the sUAS carrying the sensors was placed inside a 7.8×1.8×2.2-meter wind tunnel (Model 404B, Engineering Laboratory Design Inc.) and exposed to a range of wind speeds from 5 to 27 m s$^{-1}$ to simulate and bracket the effects of airflow over the sensors experienced during data flights with the Skywalker X8. A partial correction factor for the sensor packages that deviated from zero air speeds was obtained.

In the second set of controls, a light source was used to correct for the effects of solar irradiation on the sensor packages protected by a polylactic acid enclosure. For this purpose, a collimated 1 kW high-pressure Hg (Xe) arc lamp was employed to provide actinic radiation in the solar window after removing 1) infrared radiation with a water filter and 2) UV C light with a cutoff filter for wavelength $\lambda \geq 280$ nm. In addition, neutral density filters were employed to attenuate the light and simulate varying levels of sunlight irradiation experienced by the sensor packages in the flight field. A spectral irradiance microspectrometer (Ocean Optics) was used to determine the effective light intensity employed under various attenuations. Thus, a second partial correction factor accounting for the effect of solar irradiation was established for a range of sunlight intensities. The final overall correction factor combined the partial effects described above by correcting the data sets to an operational air speed of 18 m s$^{-1}$ and varying amount of sunlight irradiation.

Experiments for Data Collection

There were four experiments each day consisting of multiple flights. Temperature, percent relative humidity, and pressure were measured during every flight. A typical experiment lasted for about 1 h.

Data Analysis

MATLAB R2016B was used for data processing and plotting. Vertical profile gas measurements up to 120 m altitude AGL were resolved by matching the ascent/descent rate with the data logging rate, creating 40 measurements each per ascent and descent. Reported values in figures correspond to the average mixing ratio recorded every 3 m altitude, with error bars representing one standard deviation. Horizontal profiles were position resolved using the GPS measurements from the VN-300. The GPS data was block averaged to coincide with the 1 Hz logging rate of the trace gas measurements. Figures represent data points averaged every 18 m for latitude or 3 m for altitude depending on the flightpath.

Results and Discussion

This section reports data collected during 4 experiments. The physical measurements are presented first, showing the evolution of temperature and relative humidity during a single flight, and over the course of the four flights. The measurements of the trace gases: $NH_3$, CO, $NO_2$, $CH_4$, $C_3H_8$, $C_4H_{10}$, and $CO_2$ are shown later.

Physical Measurements

Measurements of temperature, pressure, and percent relative humidity were taken onboard the Skywalker X8 and DJI P3 during each flight. These variables characterize the environment during flights and facilitate the critical evaluation of sensor outputs that may be affected by varying environmental conditions.

Trace Gas Measurements

Trace gases were concurrently measured with properties onboard the Skywalker X8 and DJI P3. Seven traces gases were quantified during this campaign, $NH_3$, CO, $NO_2$, $CH_4$, $C_3H_8$, $C_4H_{10}$, and $CO_2$. These gases were measured in several flights and gathered in three different groups for practical purposes. $NH_3$, CO, and $NO_2$, were measured during one set of flights, a different set of flights measured $CH_4$, $C_3H_8$, and $C_4H_{10}$, and a third set of flights measured $CO_2$.

Seven trace gases (ammonia, carbon monoxide, nitrogen dioxide, methane, propane, butane, and carbon dioxide) were successfully quantified during the second CLOUD-MAP flight campaign in Oklahoma. The location of the site and the topography where the flights took place were typical of a rural farmland, what resulted in an optimal combination to measure environmentally relevant mixing ratios of trace gases with the Skywalker X8 and the DJI P3. Remarkably, the similar mixing ratio values registered for each gas at the same altitude (50 352 m AGL) indicates both platforms are independently robust. For example, based on the data on the integration of repeated measurements presented in Table 1, the differences between the horizontal and vertical mean mixing ratios at 50 m AGL are 0 ppbv for $NH_3$, 5.2 ppbv for CO, and 0.19 ppbv for $NO_2$, 1.3 ppbv for $CH_4$, 0.02 ppbv for $C_3H_8$, 0.04 ppbv for $C_4H_{10}$, and 1.48 ppmv for $CO_2$. In addition, to demonstrate the capability for gas detection at variable altitude, mean mixing ratios at 90 and 15 m AGL are provided together with the reference value determined at the nearby Mesonet. The agreement between the two platforms demonstrates that any effects from air speed and/or solar irradiance has been well understood and corrected to enable consistent measurements with the fixed and rotary wing sUAS. The work also serves as an example showing how this technology can be used to collect vertical and horizontal profiles of gas levels needed to 1) create a two-dimensional box model covering a slide of 120 km$^2$ per flight and 2) to measure atmospheric composition along extensive gasoducts employing sUAS to constraint the region of hydrocarbon leaking during transport.

TABLE 1

Reproducibility Analysis and Comparison to Reference Values (RV).

| | | Mean mixing ratio (ppbv, except for $CO_2$ that is in ppmv) | | | | |
|---|---|---|---|---|---|---|
| Total | | Skywalker X8 | DJI Phantom P3 | | | |
| Exp. | Gas | 50 m AGL | 50 m AGL | 90 m AGL | 15 m AGL | RV |
| 2 | $CH_4$ | 1899.8 (±5.4) | 1898.5 (±52.6) | 1855.2 (±30.1) | 1914.1 (±59.7) | 1898.4 |
| | $C_3H_8$ | 4.24 (±0.01) | 4.22 (±0.04) | 4.20 (±0.04) | 4.26 (±0.06) | 4.23 |
| | $C_4H_{10}$ | 1.60 (±0.01) | 1.64 (±0.01) | 1.61 (±0.01) | 1.66 (±0.04) | 1.59 |
| 2 | $NH_3$ | 5.58 (±0.01) | 5.58 (±0.04) | 5.59 (±0.04) | 5.58 (±0.05) | 5.58 |
| | CO | 1145.1 (±0.9) | 1150.3 (±7.2) | 1146.1 (±2.5) | 1151.0 (±6.9) | 1142.9 |
| | $NO_2$ | 35.56 ± (0.11) | 35.75 (±0.79) | 35.60 (±0.04) | 35.68 (±0.12) | 35.45 |
| 3 | $CO_2$ | 408.54 (±7.88) | 407.06 (±20.22) | 405.25 (±20.00) | 409.31 (±20.28) | 407.71 |

In addition, the sensor packages provided mixing ratios that were also in excellent agreement with reported values for this region from the Environmental Protection Agency (EPA) and/or the National Oceanographic and Atmospheric Administration (NOAA) of the United States of America. For example, the nearest Ammonia Monitoring Network (AMoN) station (36° 55' 19" N, -94° 50' 20" W) located about 209 km away detected 5.58 ppbv $NH_3$ on test day. For the case of $NO_2$, the 2016 EPA average mixing ratio for the southern region of the United States was 35.45 ppbv. The average mixing ratio of 1142.86 ppbv CO in the same EPA database. The NOAA Atmospheric Radiation Measurement (ARM) site (36° 36' 25" N, −97° 29' 20" W) about 64 km away from our field campaign site was used to compare $CH_4$, $C_3H_8$, and $C_4H_{10}$ measurements. For example, the methane, propane, and butane levels at the ARM site were 1898.48 ppbv, 4.23 ppbv, and 1.59 ppbv.

CONCLUSIONS

A major challenge in quantifying trace gases at low altitudes is the lack of available sampling techniques capable of providing measurements with a spatiotemporal resolution on the order of meters and seconds. Currently, there are not many devices that can be readily incorporated into commercially available UAVs. This work reported the creation and use of trace gas sensor packages integrated into Skywalker X8 fixed wing, and DJI P3 rotary wing, sUAS. The devices were calibrated for environmental conditions and flown at the second CLOUDMAP campaign. The results gathered through a series of example flights described the sensor package's ability to report temperature and relative humidity evolution throughout a single flight and over the course of several hours.

Furthermore, the work analyzed datasets from a typical day of 38 flights and confirmed that the fixed wing and rotary wing platforms provide similar readings, and the trace gas quantifications agree well with relevant EPA and NOAA atmospheric mixing ratios. Therefore, this work has demonstrated that these sensor packages can accurately measure temperature, relative humidity, latitude, longitude, pressure (altitude), ammonia, carbon monoxide, nitrogen dioxide, methane, propane, butane, and carbon dioxide. This device can serve as a useful tool to determine weather conditions and quantify trace gas mixing ratios, particularly at sites of greenhouse and toxic gas pollution. Future applications of this device to environmental monitoring should help to constrain the uncertainty of low altitude (<100 m) trace gas measurements without serious safety concern or extensive costs. Among the main advantages of the reported analytical platform are the short time needed from set up to deployment (just minutes), and the fact that the analysis can last for up to 1 h covering slides of 120 $km^2$ with high spatiotemporal resolution.

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled.

What is claimed:

1. A trace gas detection system, comprising:
    a first unmanned aerial vehicle (UAV) including a first sensor package having a first environmental parameter sensor for detecting current temperature, current relative humidity and current barometric pressure and a first gas sensor for detecting in real time presence of at least one gas to be monitored by the trace gas detection system;
    a second UAV including a second sensor package having a second ambient environmental parameter sensor for detecting current temperature, current relative humidity and current barometric pressure and a second gas sensor for detecting in real time the presence of said at the least one gas to be monitored by the trace gas detection system; and
    a ground station including a third sensor package having a third ambient environmental parameter sensor for detecting current temperature, current relative humidity and current barometric pressure and a third gas sensor for detecting in real time the presence of said at least one gas to be monitored by the trace gas detection system whereby gas detection is simultaneously provided at three points within an area being monitored by said trace gas detection system.

2. The trace gas detection system of claim 1, wherein said first gas sensor and said second gas sensor are configured to detect the presence of at least two of methane, propane and butane.

3. The trace gas detection system of claim 1, wherein said first gas sensor and said second gas sensor are configured to detect the presence of methane, propane and butane.

4. The trace gas detection system of claim 1, wherein said first gas sensor and said second gas sensor are configured to detect the presence of carbon dioxide and carbon monoxide.

5. The trace gas detection system of claim 1, wherein said first UAV includes a first GPS locator device providing real time location coordinates for said first UAV and said second UAV includes a second GPS locator device providing real time location coordinates for said second UAV.

6. The trace gas detection system of claim 1, wherein said first gas sensor and said second gas sensor are further configured to detect a volatile organic compound (VOC).

7. A method of monitoring an area for gas detection, comprising:
    flying a first unmanned aerial vehicle (UAV) with a first sensor package on a first flight profile through said area;
    simultaneously flying a second UAV with a second sensor package on a second flight profile through said area;
    monitoring current location of said first UAV by a first GPS locator and monitoring current location of said second UAV by a second GPS locator;
    locating a ground station with a third sensor package within said area; and
    simultaneously detecting the presence of the at least one gas of interest with said first sensor package, said second sensor package and said third sensor package whereby gas detection is simultaneously provided at three different locations within said area.

8. The method of claim 7, including providing said first profile along a first axis through said area and providing said second profile along a second, different axis through said area.

9. The method of claim 8, wherein said first axis is vertical and said second axis is horizontal.

10. The method of claim 8, further including detecting current ambient temperature, relative humidity and barometric pressure by operation of a first ambient parameter sensor on said first UAV and a second ambient parameter sensor on said second UAV.

11. The method of claim 7, further including detecting current ambient temperature, relative humidity and barometric pressure by operation of a third ambient parameter sensor on said ground station.

* * * * *